United States Patent
Williams et al.

(10) Patent No.: US 10,393,645 B2
(45) Date of Patent: Aug. 27, 2019

(54) MANUFACTURE ELECTRODES FOR ELECTROCHEMICAL MONITORING

(71) Applicant: THE BOEING COMPANY, Chicago, IL (US)

(72) Inventors: Kristen S. Williams, Madison, AL (US); Sean M. Pennell, Huntsville, AL (US); Erik D. Sapper, Ballwin, MO (US); Christina C. Grumbach, Harvest, AL (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/355,604

(22) Filed: Nov. 18, 2016

(65) Prior Publication Data

US 2018/0143126 A1    May 24, 2018

(51) Int. Cl.
G01N 17/02    (2006.01)

(52) U.S. Cl.
CPC ................... *G01N 17/02* (2013.01)

(58) Field of Classification Search
CPC ........ G01N 17/02; G01N 17/00; G01N 17/04; G01N 27/041; G01N 27/20
See application file for complete search history.

(56) References Cited

U.S. PATENT DOCUMENTS

| | | | |
|---|---|---|---|
| 5,549,803 A * | 8/1996 | Schoess ................. | G01N 17/02 204/400 |
| 5,859,537 A * | 1/1999 | Davis ..................... | G01N 17/02 204/404 |
| 6,615,671 B1 | 9/2003 | Carstensen et al. | |
| 6,911,828 B1 | 6/2005 | Brossia et al. | |
| 7,477,060 B2 | 1/2009 | Yu et al. | |
| 2007/0144272 A1* | 6/2007 | Yu ........................... | G01N 17/02 73/862.046 |
| 2017/0059472 A1* | 3/2017 | Pennell .................. | G01N 17/02 |
| 2017/0212034 A1* | 7/2017 | Sapper ................. | G01N 17/043 |

FOREIGN PATENT DOCUMENTS

DE    9309063 U1    8/1993

OTHER PUBLICATIONS

Extended European Search Report for European Application No. 16183323.1 dated Dec. 19, 2016.
A.E.A. Chemin, Effect of Saline 1-15 Corrosion Environment on Fatigue Crack Growth of 7475-T7351 Aluminum Alloy under TWIST Flight Loading, Engineering Fracture Mechanics, vol. 141, May 27, 2015, pp. 274-290.

* cited by examiner

*Primary Examiner* — Jermele M Hollington
*Assistant Examiner* — Suresh K Rajaputra
(74) *Attorney, Agent, or Firm* — Patterson + Sheridan, LLP

(57) ABSTRACT

In one aspect, a material system comprises a metal substrate and a first coating layer disposed on the metal substrate. A first electrode is directly disposed on the first coating layer, and a second electrode is disposed on the metal substrate. In one aspect, a method for determining material performance includes flexing a material system and detecting impedance of the material system with an electrochemical impedance spectrometer. The material system has a metal substrate, a first coating layer disposed on the metal substrate, a first electrode directly disposed on the first coating layer, and a second electrode disposed on the metal substrate.

11 Claims, 12 Drawing Sheets

MANUFACTURE ELECTRODES FOR ELECTROCHEMICAL MONITORING

FIELD

Aspects of the present disclosure generally relate to material systems and methods for determining operational performance of material systems.

BACKGROUND

Spanning the lifetime of operation, an aircraft will experience repeated and harsh conditions resulting in degradation of component parts of the aircraft. Such degradation may take the form of, for example, corrosion and subsequent metal fatigue and fracture. Corrosion can contribute to a decrease in the integrity and strength of aircraft components. More specifically, a material system, such as an aircraft component, includes a fuselage or skin panels, a coated lap joint between two metal panels, or a wing-to-fuselage assembly on the exterior of an aircraft. Material systems may corrode over time due to exposure to mechanical and chemical stresses during use of the aircraft. Before a material is determined to be suitable for use as an aircraft material system, it may be desirable to determine the material system's propensity to corrode. However, performance of aircraft material systems, such as panels, during actual, real world use of the aircraft seldom correlates with corrosion testing data.

Furthermore, a corrosion testing procedure of a material system comprises spraying the material system with a salt solution in a chamber. Assessment of the extent of corrosion of the material system involves stopping the corrosion procedure and removing the material system from the chamber for visual inspection to determine the extent of corrosion.

Therefore, there is a need in the art for material systems, apparatus, and methods for controlled and accurate exposure and corrosion detection for determining operational performance of material systems.

SUMMARY

In one aspect, a material system comprises a metal substrate and a first coating layer disposed on the metal substrate. A first electrode is directly disposed on the first coating layer, and a second electrode is disposed on the metal substrate.

In another aspect, a method for determining material performance comprises flexing a material system and detecting impedance of the material system with an electrochemical impedance spectrometer. The material system comprises a metal substrate and a first coating layer disposed on the metal substrate. A first electrode is directly disposed on the first coating layer, and a second electrode is disposed on the metal substrate.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this present disclosure and are therefore not to be considered limiting of its scope, for the present disclosure may admit to other equally effective aspects.

Figure 1:
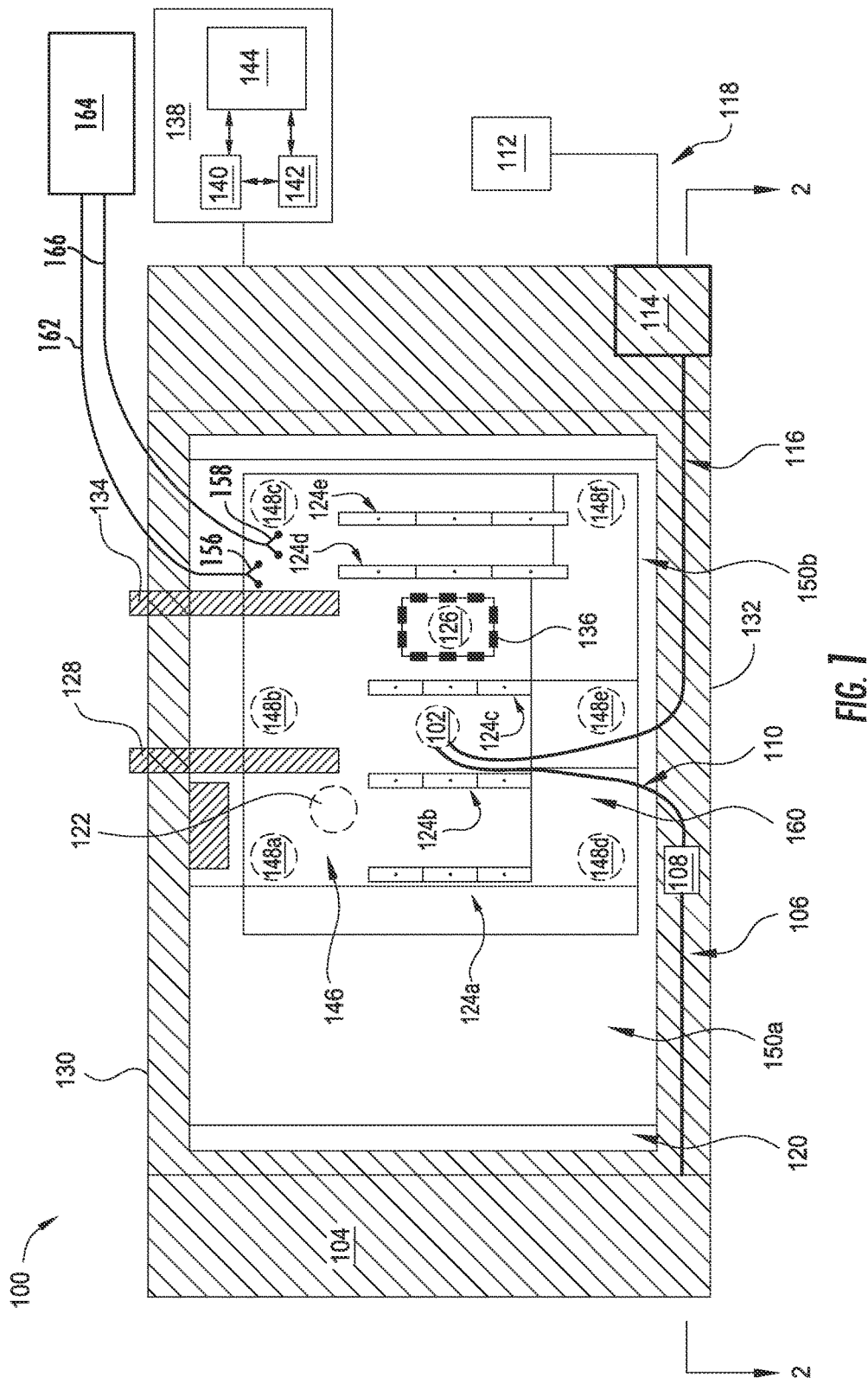
FIG. 1 is a top sectional view of an apparatus for accelerating and controlling the corrosion-related failure modes of a material system, according to an aspect of the disclosure.

To facilitate understanding, identical reference numerals have been used, where possible, to designate identical elements that are common to the figures. The figures are not drawn to scale and may be simplified for clarity. It is contemplated that elements and features of one aspect may be beneficially incorporated in other aspects without further recitation.

DETAILED DESCRIPTION

The descriptions of the various aspects of the present disclosure have been presented for purposes of illustration, but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects disclosed herein.

Aspects of the present disclosure generally relate to material systems and methods for determining operational performance in situ of material systems. A material system can be a component of an aircraft and typically comprises a substrate, such as a metal, and one or more coatings, such as an epoxy, disposed on the substrate. One or more electrodes, such as a pair of electrodes, are disposed on or within a surface of the material system to provide electrochemical detection of operational performance, e.g. corrosion, of the material system. Determining operational performance of a material system can be performed in a lab setting or on an aircraft by an operator or manufacturer before, during (in situ), or after the material system has been exposed to flexing and/or moisture treatment. For example, a material system is in electrical communication with a spectrometer to provide impedance data of one or more surfaces of the material system to assist in determination of the operational performance of the material system during flexing and moisture exposure of the material system.

Apparatus

A material system, such as a panel, may have one or more surface layers such as a surface finish, a primer, and/or a top coat. Corrosion may occur at one or more of these layers in use due to mechanical and chemical stresses. Material systems, apparatus, and methods of the present disclosure provide in situ electrochemical monitoring of impedance to determine corrosion in a setting that mimics the corrosion experienced by a material system in actual use conditions. The material system is subjected to mechanical as well as chemical stresses without degradation of the electrochemical monitoring system. Material systems, apparatus and methods of the present disclosure provide electrochemical monitoring of impedance to determine corrosion at one or more of a material system surface, a finished surface, a primer surface, and/or a top coat surface.

Figure 2:
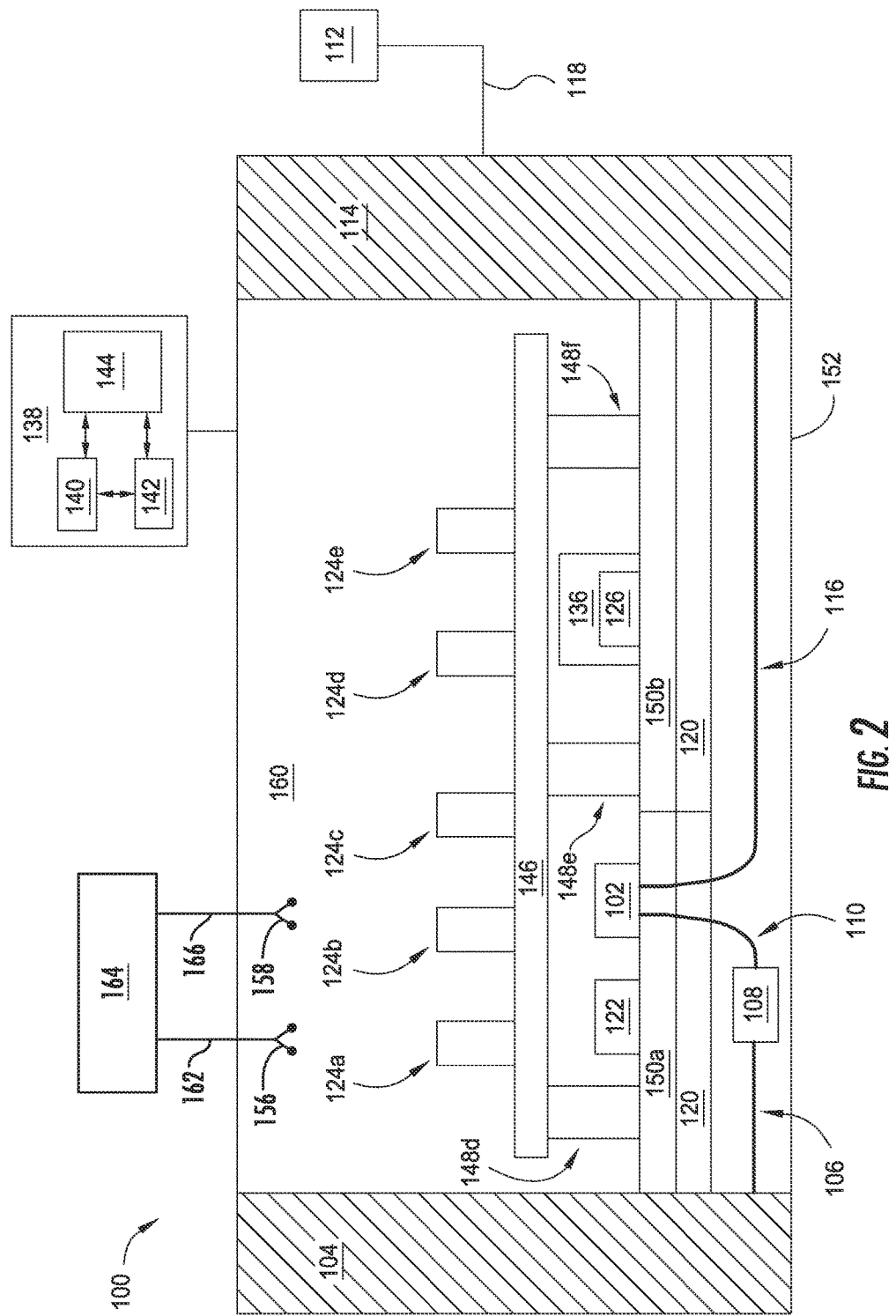
FIG. 2 is a side sectional view of an apparatus for accelerating and controlling the corrosion-related failure modes of a material system, according to an aspect of the disclosure.
Figure 3:
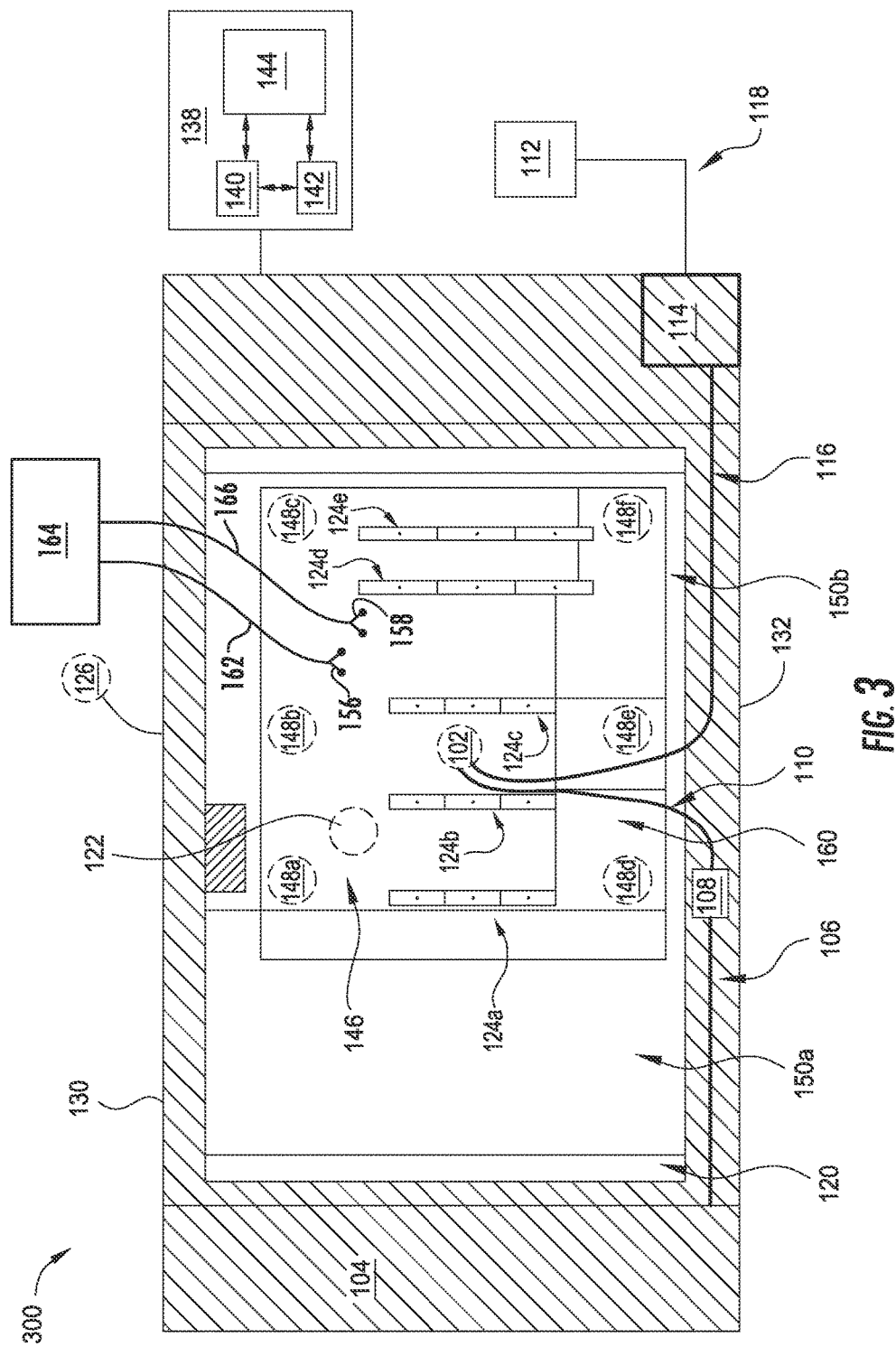
FIG. 3 is a top sectional view of an apparatus for accelerating and controlling the corrosion-related failure modes of a material system, according to an aspect of the disclosure.
Figure 4:
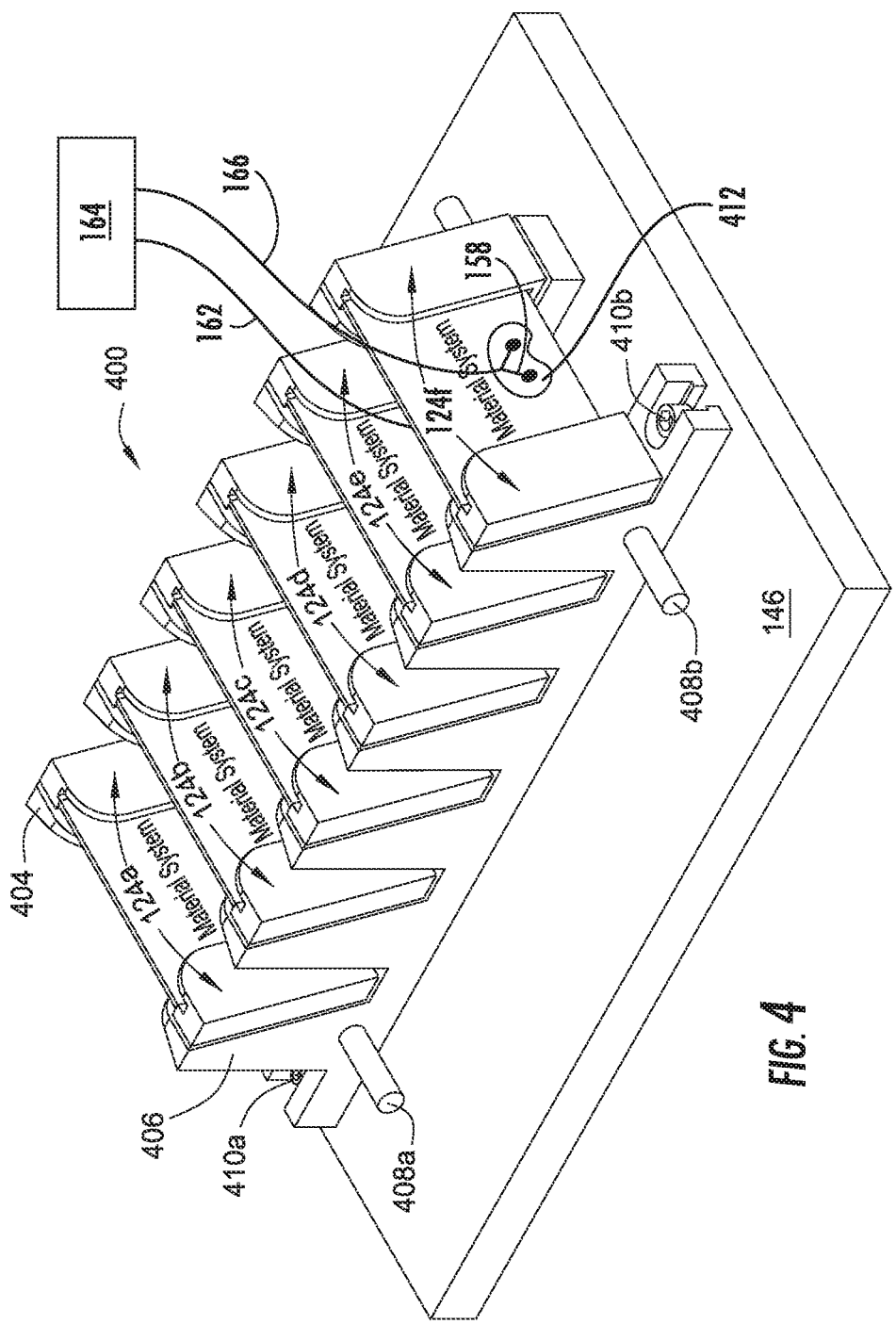
FIG. 4 is a perspective view of a flexer configured to perform cyclic flexing, according to an aspect of the disclosure.

FIG. 1 is a plan view of an apparatus 100 for accelerating and controlling the corrosion-related failure modes of a material system, according to an aspect of the disclosure. FIG. 2 is a side perspective view of apparatus 100 of FIG. 1. One or more components of apparatus 100 are made of materials that show resistance to a corrosive environment, such as an environment containing a salt fog. As shown in FIGS. 1 and 2, apparatus 100 includes an enclosure 160 having one or more fog nozzles 102 (one shown) disposed therein and configured to spray a treating liquid, such as a salt fog, in the enclosure 160. A fixture support is disposed in the enclosure to support a material system for exposure and flexing therein. Apparatus 100 includes a liquid reservoir 104 to supply a treating liquid to fog nozzle 102. Fog nozzle 102 may be a nozzle, such as an atomizing nozzle, a nozzle calibrated for air consumption, BETE full cone nozzle, hollow cone nozzle, fan misting nozzle, tank washing spray nozzle, NASA Mod1 nozzle for water spray atomization and droplet control, Q-Lab OEM fogging nozzle, Cool Clean ChilAire Lite spray applicator nozzle, or combinations thereof. Fog nozzle 102 can be made of materials such as hard rubber, plastic, or other inert materials.

The fixture support comprises jaws 124a-e configured to flex a material system. Plate 146 is configured to support jaws 124a-e. In at least one aspect, plate 146 comprises a mounting plate disposed on an I-Beam grate. Plate 146 is positioned between fog nozzle 102 and jaws 124a-124e (as shown in FIGS. 1 and 2), allowing treating liquid to enter the enclosure without directly impinging upon a material system held by one or more jaws 124a-e. This configuration mimics general humid atmospheric conditions, as compared to direct rainfall onto an aircraft material system. Alternatively, jaws 124a-e may be positioned between fog nozzle 102 and plate 146 (this configuration not shown), providing direct flow of treating liquid toward a material system held by one or more jaws 124a-e. This configuration mimics direct rain fall or aerosol deposition onto an aircraft material system. Fog nozzle 102 may be configured for flow angle adjustment, allowing flow of treating liquid at one or more angles relative to a material system surface. In at least one aspect, a material system surface may be parallel to a principal direction of flow of liquid through apparatus 100, based upon the dominant surface being tested, which reduces liquid collection on a material system during corrosion testing performed in apparatus 100. In such aspects, fog nozzle 102 may be directed or baffled so that the liquid does not impinge directly on a material system. (Fog nozzle 102, a vent 122, a motor 126, an outer enclosure 136, and legs 148a-f are shown as dashed lines in FIG. 1 to indicate that these parts are located behind a plate 146 in the aspect shown in FIG. 1).

A fog pump 108 is configured to assist flow of a liquid from liquid reservoir 104 to fog nozzle 102 via first fluid line 106 and second fluid line 110. First fluid line 106 couples liquid reservoir 104 at a first end with fog pump 108 at a second end to provide liquid communication of liquid reservoir 104 with fog pump 108. Second fluid line 110 couples fog pump 108 at a first end with fog nozzle 102 at a second end to provide liquid communication of fog pump 108 with fog nozzle 102.

A compressed air source 112 and bubble tower 114 are configured to provide humidified air to fog nozzle 102. In at least one aspect, a pressure in the enclosure may be regulated to mimic the pressure experienced by an aircraft at various altitudes during real world use. Accordingly, compressed air source 112 is configured to flow air at a pressure ranging from about 2 pounds per square inch (PSI) to about 50 PSI, from about 5 PSI to about 30 PSI, from about 12 PSI to about 18 PSI. In these ranges, lower pressure values mimic pressures experienced by an aircraft at higher altitudes while higher pressure values mimic pressures experienced by an aircraft at lower altitudes and closer to sea level. Air may include a mixture of gases similar to that found in an ambient atmosphere, for example, comprising about 78% $N_2$, about 21% $O_2$, and about 0.039% $CO_2$, among other gases. Third fluid line 116 couples bubble tower 114 at a first end with fog nozzle 102 at a second end to provide air and liquid communication of bubble tower 114 with fog nozzle 102. A compressed air line 118 couples compressed air source 112 at a first end with bubble tower 114 at a second end to provide air communication of compressed air source 112 with bubble tower 114. Bubble tower 114 may contain a liquid, such as water, to provide initial humidification or additional humidification to air flowed from compressed air source 112 via compressed air line 118.

A vent 122 may be coupled with the first chamber wall 130, a second chamber wall 132, or a third wall 152 (FIG. 2) to provide pressure regulation inside of apparatus 100. A heater 120 may be provided and configured to heat the inside of apparatus 100 such as enclosure 160. Heater 120 may be disposed adjacent to a first wall 130 of apparatus 100 and coupled with third wall 152 (FIG. 2). Heater 120 may be adhered to third wall 152 by any suitable adherent, such as rivets. Heater 120 may be coupled with and controlled by controller 138.

Fixture support is configured to support and flex a material system positioned in the enclosure for testing. Jaws 124a, 124b, 124c, 124d, and 124e are configured to flex a material system, such as a panel, a coated lap joint between two metal panels, a wing-to-fuselage assembly, or combinations thereof. The material system may be an aircraft material system, such as a panel, such as a skin or fuselage flat panel. The material system may have a width that is, for example, about 4 inches, and a length that is for example, about 6 inches to about 14.5 inches. The fixture support may flex a material system to a strain ranging from about 0.05% to about 50%, about 0.1% to about 30%, about 0.3% to about 5%, such as about 0.37%.

Fixture support comprising one or more jaws 124a-e is configured to grip and release a material system. Jaws 124a-e are configured to flex a material system from a first starting position to a fully or partially flexed second position. Jaws 124a-e are configured to flex a material system from a first position to greater than 0° to about 180° from the starting position, such as about 5° to about 90°, such as about 5° to about 45°, during a flexing process. Jaws 124a-124e may be the same size or different sizes. For example, jaw 124a may be the same size as jaw 124b, but be a different size than jaw 124d (as shown in FIG. 1). Furthermore, jaws 124a-124e may be positioned from one another by a distance that is the same or different than a distance between a different pair of jaws 124a-e. For example, a first distance between jaw 124a and 124b may be different than a second distance between jaw 124d and 124e. Various jaw sizes and various distances between jaws provide, for example, simultaneous testing of different sized material systems, such as panels, during an exposing and flexing process within apparatus 100. In at least one aspect, one or more of jaws 124a-e comprises steel. In at least one aspect, one or more of jaws 124a-e is anodized. In at least one aspect, one or more of jaws 124a-e comprises an inert material such as hard rubber and/or plastic. In at least one aspect, jaws 124a-e are configured to support a material system, such as a panel, from about 15° and about 30° relative to a first wall 130 and/or second wall 132, which reduces liquid collection on a material system during corrosion testing performed in apparatus 100. In at least one aspect, jaw 124a is configured to grip a material system at a first end of the material system and jaw 124b is configured to grip the material system at a second end of the material system. In at least one aspect, jaws 124a-e are configured to flex a material system simultaneously or alternatively.

A motor 126 operates jaws 124a-e. Inlet tube 128 is coupled with motor 126 at a first end and coupled with first wall 130 at a second end for providing cooling material, such as air, to motor 126. Outlet tube 134 is coupled with motor 126 at a first end and coupled with first wall 130 at a second end for removing hot air exhaust from motor 126. Outer enclosure 136 surrounds motor 126 to enclose and protect the motor from liquid emitted from fog nozzle 102 or any other liquid present inside of apparatus 100. Jaws 124a-e are supported by plate 146. Plate 146 is supported by legs 148a, 148b, 148c, 148d, 148e, and 148f. Legs 148a-f are coupled with plate 146 at a first end and a chamber wall, a rack 150a, or a rack 150b at a second end.

Apparatus and material systems of the present disclosure include one or more electrodes, such as one or more pairs of electrodes. An electrode may be coupled with a substrate (to form a material system) and subsequent use of apparatus 100 to test operational performance of the material system. During flexing, the center portion of the material system will experience more strain than the edges of the material system. Accordingly, a pair of electrodes disposed on the same side of the material system provides detecting impedance across the same side of the material system.

As shown in FIGS. 1 and 2, apparatus 100 includes electrode pairs 156 and 158. Although electrode pairs are shown in FIGS. 1 and 2, in an alternative aspect, apparatus 100 comprises single electrodes. Electrode pair 156 is configured to couple with a first side of a material system (not shown), and electrode pair 158 is configured to couple with a second side of the material system (not shown). Electrodes can be made of conductive epoxy, gold, silver, copper, platinum, palladium, or mixtures thereof. Preferably, at least one electrode is conductive epoxy, such as the electrodes of pairs 156 and/or 158. In at least one aspect, conductive epoxy is conductive silver epoxy. Electrode pair 156 is coupled with spectrometer 164 via electrical line 162 to provide electrical communication between electrode pair 156 and spectrometer 164. Furthermore, electrode pair 158 is coupled with spectrometer 164 via electrical line 166 to provide electrical communication between electrode pair 156 and spectrometer 164. Electrical lines 162, 166 can be insulated wire (e.g., insulated steel wire) or wire having insulated conductive tape. Electrode pair 156 is configured to couple with a first side of a material system, and electrode pair 158 is configured to couple with a second side of the material system, as described in more detail below. In at least one aspect, spectrometer 164 comprises a potentiostat, galvanostat, and/or zero-resistance ammeter. Spectrometer 164 can be an electrochemical impedance spectrometer, such as a Reference600 supplied by Gamry Instruments or a VMP300 supplied by Bio-Logic Science Instruments. When coupled with a material system, electrodes (e.g., electrode pairs 156 and 158) detect an electrical signal from the material system and transmit the electrical signal to a spectrometer, such as spectrometer 164. Spectrometer 164 is configured to interpret the electrical signal to provide electrical data, such as impedance, regarding the condition, such as corrosion, of the material system. Electrochemical impedance is usually measured by applying an AC potential to an electrochemical cell and then measuring the current through the cell. The response to this [sinusoidal] potential is an AC current signal. This current signal can be analyzed as a sum of sinusoidal functions (a Fourier series). Electrochemical impedance is normally measured using a small excitation signal. This is done so that the cell's response is pseudo-linear. In a linear (or pseudo-linear) system, the current response to a sinusoidal potential will be a sinusoid at the same frequency but shifted in phase. EIS data are typically analyzed in terms of an equivalent circuit model. Echem Analyst [a Gamry software product] finds a model whose impedance matches the measured data.

Parts of apparatus 100 described herein may comprise materials that are suitably inert to conditions within apparatus 100 during a cyclic flexing fog spray process. Suitably inert materials may include plastic, glass, stone, metal, rubber, and/or epoxy.

Apparatus 100 may be controlled by a processor based system controller such as controller 138. For example, the controller 138 may be configured to control apparatus 100 parts and processing parameters associated with a cyclic flexing fog spray process. The controller 138 includes a programmable central processing unit (CPU) 140 that is operable with a memory 142 and a mass storage device, an input control unit, and a display unit (not shown), such as power supplies, clocks, cache, input/output (I/O) circuits, and the like, coupled to the various components of the apparatus 100 to facilitate control of a cyclic flexing fog spray process. Controller 138 may be in electronic communication with, for example, outlet tube 134, vent 122, heater 120, and/or jaws 124a-e.

To facilitate control of the apparatus 100 described above, the CPU 140 may be one of any form of general purpose computer processor that can be used in an industrial setting, such as a programmable logic controller (PLC), for controlling various chambers and sub-processors. The memory 142 is coupled to the CPU 140 and the memory 142 is non-transitory and may be one or more of readily available memory such as random access memory (RAM), read only memory (ROM), floppy disk drive, hard disk, or any other form of digital storage, local or remote. Support circuits 144 are coupled to the CPU 140 for supporting the processor in a conventional manner. Information obtained from cyclic flexing fog spray processes with apparatus 100 may be stored in the memory 142, typically as a software routine. The software routine may also be stored and/or executed by a second CPU (not shown) that is remotely located from the hardware being controlled by the CPU 140. The memory 142 is in the form of computer-readable storage media that contains instructions, that when executed by the CPU 140, facilitates the operation of the apparatus 100. The instructions in the memory 142 are in the form of a program product such as a program that implements the method of the present disclosure. The program code may conform to any one of a number of different programming languages. In at least one aspect, the disclosure may be implemented as a program product stored on computer-readable storage media for use with a computer system. The program(s) of the program product define functions of the aspects (including the methods described herein). Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored. Such computer-readable storage media, when carrying computer-readable instructions that direct the functions of the methods and apparatus of the present disclosure, are aspects of the present disclosure.

FIG. 3 is a plan view of an apparatus 300 for accelerating and controlling the corrosion-related failure modes of a material system, according to an aspect of the disclosure. As shown in FIG. 3, the components of apparatus 300 are the same as the components shown in apparatus 100 of FIG. 1, except that motor 126 is not encompassed by outer enclosure 136 (outer enclosure 136 is not present), motor 126 is located external to first chamber wall 130, and inlet tube 128, and outlet tube 134 are not present. Motor 126 is coupled with first chamber wall 130. In at least one aspect, motor 126 (coupled to first chamber wall 130) translates bending motion inside the chamber via a screw, such as a ball screw, Acme screws, Lead screws, Roller screws, and screw mount, or an axle, passing into the chamber (not shown). A screw maintains spacing between stationary block 406 and mobile block 404 during flexing.

FIG. 4 is a perspective view of a flexer 400 configured to perform cyclic flexing, according to an aspect of the disclosure. Flexer 400 may be located inside of a material performance chamber, such as apparatus 100 as described for FIG. 1. As shown in FIG. 4, flexer 400 includes a mobile block 404 and a stationary block 406. Stationary block 406 is mounted to plate 146 by mounting bolts 410*a* and 410*b*. Mobile block 404 is slidably disposed on plate 146 adjacent to stationary block 406. Linear displacement between stationary block 406 and mobile block 404 is maintained by guide rods 408*a* and 408*b*. Guide rods 408*a* and 408*b* may comprise stainless steel, high density polypropylene, high density polyethylene, chromium, such as an Armology coating, and combinations thereof. Each of guide rods 408*a* and 408*b* is coupled with stationary block 406 and mobile block 404. Guide rods 408*a* and 408*b* are parallel to one another. Stationary block 406 and mobile block 404 mount or otherwise support jaws 124*a-f*. Stationary block 406 mounts a first side of jaws 124*a-f* in a stationary position during flexing, while mobile block 404 mounts a second side of jaws 124*a-f* and allows movement of the second side of jaws 124*a-f* during flexing. Stationary block 406 and mobile block 404 may comprise high density polyethylene. During flexing, the mobile block is shifted laterally relative to the stationary block from a starting point to an end point resulting in flexing of the material system positioned in jaws 124*a-f*. The starting point, end point, and shift distance may be controlled by a user of flexer 400 based on test fixture mechanical boundary limits, mechanical stop blocks, or fixture driving system software controls. Each of stationary block 406 and mobile block 404 includes a base and a plurality of stanchions extending from the base perpendicular thereto. Each stanchion may be rectangular or angled to provide an angle on which each of the jaws 124*a-f* can be mounted. Jaws 124*a-f* are hinged, which allows bending of a material system while compressing the material system. For example, jaws 124*a-f* may be mounted on one side of each stanchion and disposed at an angle from, for example, 15° to 30° relative to a line perpendicular to the base. Other angles relative to perpendicular are contemplated to achieve a desired testing condition for a material panel. The angle of jaws 124*a-f* determines the angular position of the material system. In at least one aspect, a material system is disposed at an angle from, for example, 15° to 30° relative to a line perpendicular to the base. In at least one aspect, jaws 124*a-f* are non-conductive and non-metallic so as to have little or no galvanic effect on the material system. One or more of jaws 124*a-f* may comprise high density polyethylene, commercial grade Titanium (II) with polyethylene insert, sacrificial 316SS with polyethylene insert, or combinations thereof, which prevents (partial or complete) galvanic corrosion of the jaws and material systems during testing. One or more of jaws 124*a-f* may comprise a sleeve cover comprising, for example, polyethylene, which further prevents galvanic corrosion of the jaws and material systems during testing. Electrode pair 158 of apparatus 100 is directly disposed on a first side of a material system disposed in jaw 124*f*, and electrode pair 156 (not shown) of apparatus 100 is disposed on a second side of the material system opposite the first side. A non-conductive protective coating 412 (shown as a transparent coating for simplicity) is disposed on electrode pairs 158 and 156 to protect the electrodes from a corrosive environment while apparatus 100 is in use, e.g. testing the material system. Non-conductive protective coatings include non-conductive epoxy, tape, adhesive, sealant, or mixtures thereof. In at least one aspect, non-conductive epoxy is a 2-part waterproof epoxy. Although FIG. 4 shows electrodes directly disposed on a material system disposed in jaw 124*f*, it is to be understood that material systems (and apparatus) of the present disclosure embrace aspects where one or more electrodes and/or electrode pairs are directly disposed on material systems disposed in one or more of jaws 124*a-e*, and the electrodes and/or electrode pairs can be in electrical communication with spectrometer 164 via electrical lines similar or identical to electrical lines 162, 166. Such aspects provide electrochemical in situ monitoring of a plurality of material systems within a material performance chamber, such as apparatus 100. Furthermore, a non-conductive protective coating, such as coating 412, can be disposed on said electrodes and/or electrode pairs.

In at least one aspect of the present disclosure, a material performance chamber contains more than one flexer 400. In at least one aspect where a material performance chamber contains more than one flexer 400, guide rods 408a and 408b extend through multiple flexers 400.

A flexer, such as flexer 400, provides variable displacement of a mobile block and material systems at variable frequencies that are adjustable in real-time. A flexer also provides for application of tension and compression to a material system.

Material Systems

In at least one aspect, a material system is a metal panel that can be flat and can be coated. The material performance of the flat panel is tested by cyclically flexing the material system while exposing the panel to at least a cycle of salt fog. Before, during, and/or after exposure and flexing, the material system is assessed for corrosion onset, rate of propagation, and performance.

In at least one aspect, a material system comprises a substrate having two flat metal panels connected, joined, welded, bonded, or fastened together using metallic fasteners, screws, bolts, or other hardware, before being exposed to at least a cycle of salt fog.

In at least one aspect, a material system comprises a mechanical joint or knuckle joint that may be made of metallic or composite materials and coated before being exposed to a cyclic salt fog and/or before being assessed for corrosion onset, rate of propagation, and performance.

In at least one aspect, a material system comprises a structural system replicative of aircraft components, representing a side-of-body joint, a stringer-to-fuselage assembly, a fuselage panel, or wing spar-to-fuselage assembly. The produced assemblies may be actuated or flexed while being exposed to at least a cycle of salt fog before/while being assessed for corrosion onset, rate of propagation, and performance, as described herein.

Figure 5:
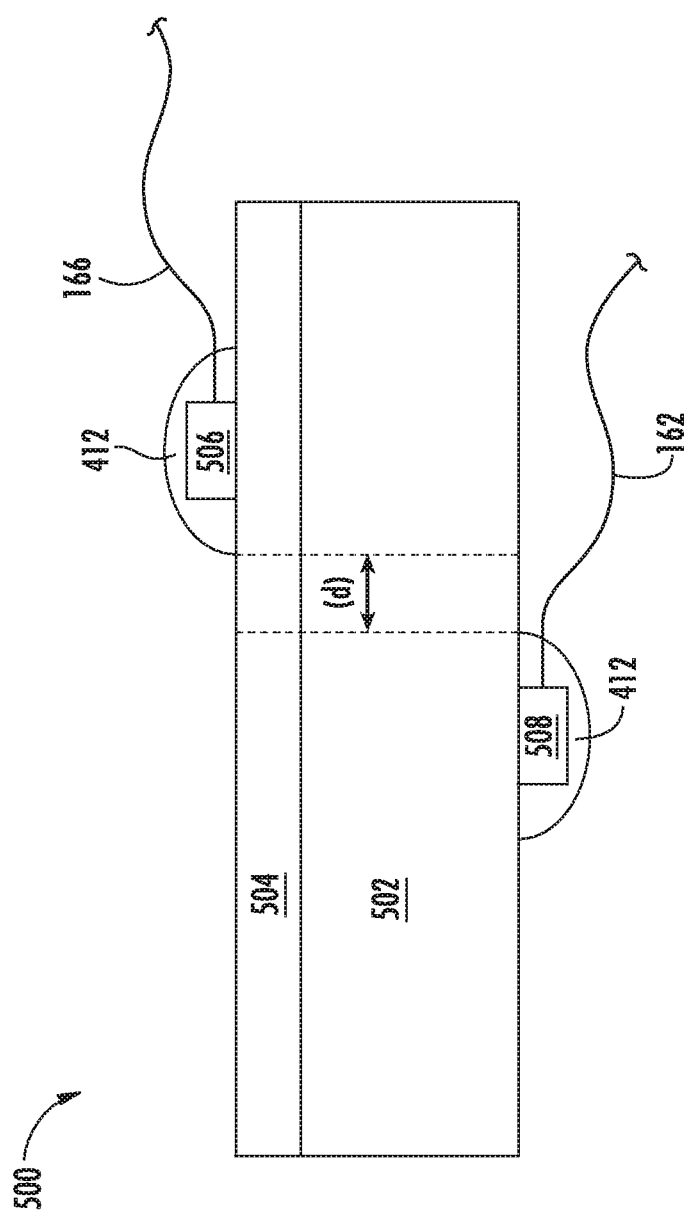
FIG. 5 is a side view of a material system, according to an aspect of the disclosure.

FIG. 5 is a side view of a material system 500 depicting material system 500 comprising a conductive metal substrate 502 and a coating layer 504 disposed on substrate 502. Metal substrate 502 can be made of titanium, aluminum, copper, or alloys thereof. Metal substrate 502 may be coated with one or more primers, such as a chromated primer, surface finishes and/or top coats. For example, coating layer 504 can be made of chromated primer, epoxy primer, urethane primer, or mixtures thereof. Electrode 506 (which can be part of an electrode pair such as electrode pair 158) is directly disposed on coating layer 504 and is a reference electrode. Electrode 508 (which can be part of an electrode pair such as electrode pair 156) is disposed on the metal substrate 502 and is a working electrode. In at least one aspect, an insulating adhesive, such as non-conductive epoxy, is disposed between electrode 508 and metal substrate 502. For spectroscopic measurements during testing, the working electrode 508 is adhered to conductive metal substrate 502, and an electrical signal is sent through the working electrode (or pair of electrodes). The signal then moves through coating layer 504 and is received by electrode 506 (of electrode pair 158) and transmitted to spectrometer 164. In an alternative aspect, working electrode 508 and reference electrode 506 is each disposed (e.g., directly disposed) on coating layer 504.

In aspects where a coating layer, such as coating layer 504, is made of an epoxy and an electrode disposed on the coating layer is made of a conductive epoxy, it has been discovered that the epoxy materials of the coating layer and the electrode absorb to one another. Use of an adhesive to adhere the two materials together is optional such that the electrode is directly disposed on the coating layer. In such aspects, a surface of the coating layer can be lightly abraded, followed by applying the electrode directly to the abraded surface. This "like-on-like" interaction between coating layer and electrode improves compatibility of the interface of the electrode and coating layer. The improved compatibility between the electrode and coating layer improves thermal and mechanical properties between the coating layer and the electrode. Conventional electrodes are adhered to a substrate surface with non-conductive adhesives. These adhesives interfere with the electrical communication of the electrode and a substrate such as a coating layer, yielding inaccurate spectroscopic data. With use of such adhesives, the electrical properties of the material system are being affected by a component (the adhesive) that is not a component of a material system that would be used in commercial applications. The adhesive causes a sharp gradient in mechanical, chemical, and thermal performances of the material system where the electrode is located. The improved compatibility between electrodes and coating layers of material systems of the present disclosure provides homogeneity between the electrodes and coating layers yielding reduced noise observed in a spectroscopic signal.

As a comparative example to material systems having epoxy electrodes, a material system having metal electrodes deposited onto a coating layer was tested. Electrochemical monitoring of the material system having metal electrodes deposited onto a coating layer provided an EIS spectrum showing only an "air" curve, indicative of an insufficient interaction between the metal electrodes and the coating layer. As used herein, "air curve" indicates an open-lead experiment. This experiment records an EIS spectrum with no cell attached. The spectrum from an open-lead experiment looks very much like a noisy spectrum for a parallel RC network. So, when an air curve is observed in the data, the leads from the spectrometer are not making electrical contact with the coating, and an EIS spectrum of the open air (i.e. an "air curve) is being collected.

Furthermore, it has been discovered that the thickness of electrodes of a material system can affect spectroscopic results of electrochemical monitoring. Electrodes of the present disclosure, such as electrodes 506 and 508 of electrode pairs 156 and/or 158, can have a thickness of about 12 micrometers (μm) or less. Electrodes having a thickness of about 12 μm or less provide flexibility of the electrodes disposed on and/or within a material system and provide material systems operable to have an electrode disposed on one or more layers of the material system for more accurate electrochemical monitoring of each of the one or more layers of a material system. In at least one aspect, electrodes of the present disclosure have a thickness of from about 1 μm to about 12 μm, such as from about 2 μm to about 11 μm, such as from about 3 μm to about 10 μm. In at least one aspect, a coating layer of the present disclosure has a thickness of from about 1 μm to about 500 μm, such as from about 2 μm to about 250 μm, such as from about 3 μm to about 100 μm, such as from about 4 μm to about 15 μm. Furthermore, the reduced size of the electrodes of the present disclosure provides smaller/thinner electrical wires (coupled with the electrodes at a first end and a spectrometer at a second end) to be used for material systems of the present disclosure, as compared to traditional electrical wires that are too large to be embedded within layers of a multilayered material system.

In comparison, an electrode having a thickness of 13 μm or greater (such as interdigitated electrodes) is more rigid than thinner electrodes and tends to disconnect from the material system during flex testing. The rigidity of thick electrodes hinders the electrode's ability to conform to a surface of the material system. Furthermore, if a conventionally thin coating layer (such as an assembly primer, interior primer, fuel tank primer) is disposed on an electrode, electrodes having a thickness of 13 μm or greater tend to create a defect in the overlying layer and the defect is then accentuated over the course of flex testing. Furthermore, some conventional electrode designs involve drilling through the substrate to embed electrodes within a layer. Such embedded electrodes have similar drawbacks as described for thick electrodes.

In at least one aspect, electrodes of a material system of the present disclosure are offset from one another. For example, as shown in FIG. 5, electrodes 506 and 508 are offset from one another by a distance (d). Offsetting the electrodes of material systems of the present disclosure reduces moisture effects because an electrical signal flows where the electrons have the least resistance. If the electrodes are not offset from one another, then the area under the reference electrode is shielded from absorbing electrolyte from moisture. As moisture content within a coating increases (e.g., in the cracks/crevices) during testing, the accuracy of electrical data is improved because of the relatively high dielectric constant of water and saline as compared to the dielectric constant of most intact coatings. Preferably, the electrodes themselves are protected from moisture or the electrical signal may be inaccurate. Protecting an electrode from moisture may be accomplished by sealing an electrode with a protective coating, such as a non-conductive epoxy.

Figure 6:
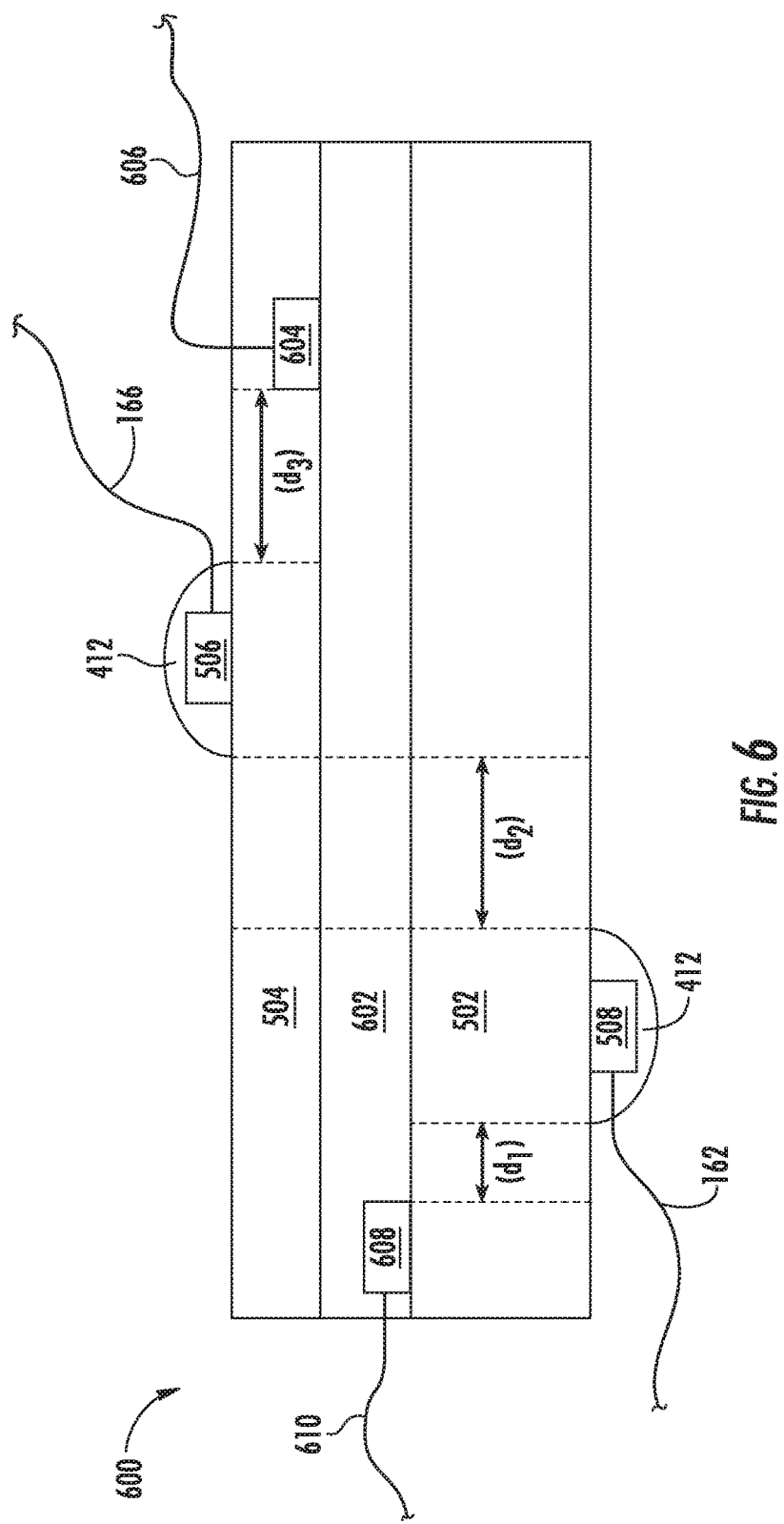
FIG. 6 is a side view of a material system, according to an aspect of the disclosure.

FIG. 6 is a side view of a material system 600, according to an aspect of the present disclosure. As shown in FIG. 6, material system 600 is a multilayered material system comprising metal substrate 502, a first coating layer 602, and a second coating layer 504. Electrode 608 (which can be of an electrode pair) is disposed on metal substrate 502 and is in electrical communication with a spectrometer, such as spectrometer 164, via electrical line 610. Furthermore, electrode 604 (which can be of an electrode pair) is disposed on first coating layer 602 and is in electrical communication with a spectrometer, such as spectrometer 164, via electrical line 606. A protective coating (not shown), such as coating 412, can be disposed on one or both of electrodes 608 and 604 before depositing a subsequent coating layer onto the electrodes and substrate. As shown in FIG. 6, electrodes 608 and 604 are internal to (e.g., embedded) the material system. Internal electrodes provide in situ electrochemical monitoring of individual layers of a material system at a coating/substrate interface of a multilayered material system to determine corrosion. In at least one aspect, an insulating adhesive, such as non-conductive epoxy, is disposed between electrode 608 and metal substrate 502.

As shown in FIG. 6, electrode 608 and electrode 508 are offset by a distance ($d_1$). Electrode 508 and 506 are offset by a distance ($d_2$). Electrode 506 and electrode 604 are offset by a distance ($d_3$). ($d_1$), ($d_2$), and ($d_3$) are sized to prevent polarizing an electrode, which would otherwise move away from the pseudo-linear portion of a voltage-current response curve. In at least one aspect, ($d_1$)=($d_2$)=($d_3$). In at least one aspect, ($d_1$), ($d_2$), and/or ($d_3$) is between about 0.3 cm and about 10 cm, such as between about 0.5 cm and about 3 cm, for example about 1 cm.

Furthermore, varying the surface area of a surface of an electrode that contacts an underlying surface affects the electrochemical interaction of the electrode with the underlying surface. One way to take advantage of varying the surface area for a desired application is to vary the shape of one or more electrodes because, other parameters being equal, different shapes result in different surface areas of a contact surface of the electrode, as explained in more detail below. Electrodes of material systems of the present disclosure can have a variety of shapes. For example, an electrode of the present disclosure is square shaped. Alternatively, an electrode of the present disclosure has a shape selected from circular, star, rectangular, or polygonal, such as pentagonal, hexagonal, heptagonal, or octagonal. Furthermore, electrodes of the present disclosure may have one or more spokes extending (e.g., outwardly) from the shape.

An electrode of the present disclosure has a surface area (including spokes if present) that contacts an underlying layer (i.e., a contact surface area) that is suitable for a desired application. In at least one aspect, an electrode has a contact surface area from about 0.2 $cm^2$ to about 10 $cm^2$, such as from about 0.5 $cm^2$ to about 5 $cm^2$, such as from about 1 $cm^2$ to about 2 $cm^2$. The overall shape, spokes, and surface area can affect electrochemical monitoring methods for a particular testing application of the present disclosure.

Figure 7C:
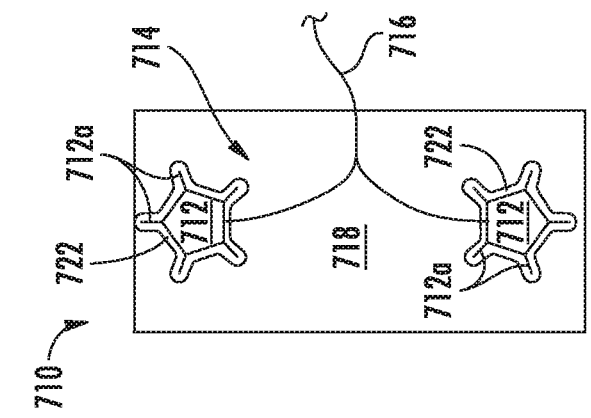
FIG. 7C is a plan view of a material system according to an aspect of the disclosure.
Figure 7B:
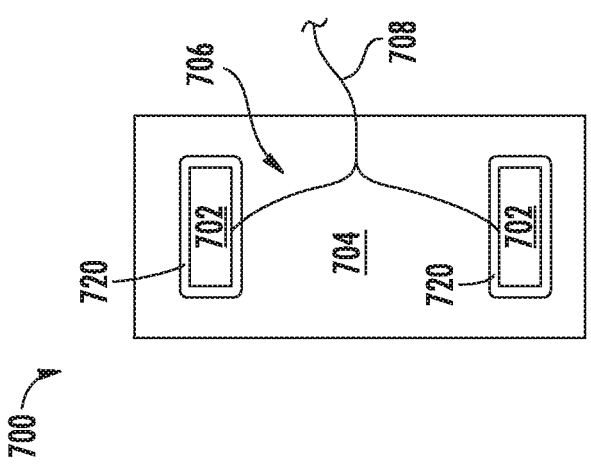
FIG. 7B is a plan view of a material system according to an aspect of the disclosure.
Figure 7A:
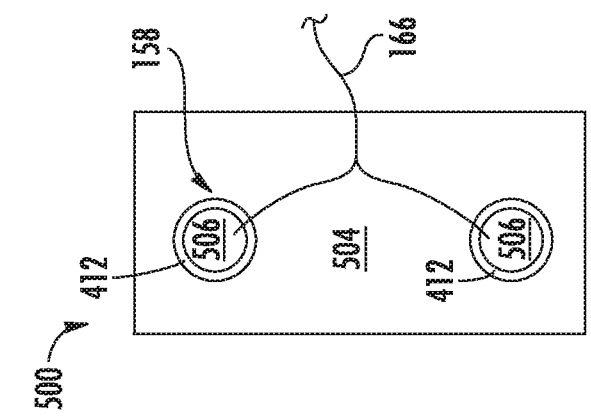
FIG. 7A is a plan view of a material system according to an aspect of the disclosure.

Each of FIGS. 7A, 7B, and 7C is a plan view of a material system according to an aspect of the present disclosure. As shown in FIG. 7A, material system 500 (of FIG. 5) comprises electrode pair 158 comprising electrodes 506 having a circular shape. Protective coating 412 is disposed on electrodes 506. In at least one aspect, protective coating 412 is also disposed on electrical wire 166 (not shown) to further protect wire 166 during flexing and/or salt fog exposure. As shown in FIG. 7B, material system 700 comprises electrode pair 706 comprising electrodes 702 having a rectangular shape. Each of electrodes 702 is disposed on material layer 704. Protective coating 720 (shown as transparent for clarity) is disposed on electrodes 702. In at least one aspect, protective coating 720 is also disposed on electrical wire 708 (not shown) to further protect wire 708 during flexing and/or salt fog exposure. Each of electrodes 702 can be in electrical communication with a spectrometer via electrical line 708. As shown in FIG. 7C, material system 710 comprises electrode pair 714 comprising electrodes 712 having a pentagonal shape. Each of electrodes 712 has five spokes 712a extending outwardly from the pentagonal shape of electrodes 712. Each of electrodes 712 is disposed on material layer 718. Protective coating 722 (shown as transparent for clarity) is disposed on electrodes 712/712a. In at least one aspect, protective coating 722 is also disposed on electrical wire 716 (not shown) to further protect wire 708 during flexing and/or salt fog exposure. Electrodes 702 can be in electrical communication with a spectrometer via electrical line 716.

Fabricating Material Systems

Fabricating a material system of the present disclosure can include lightly abrading an area of a coating layer that the electrode will be applied to. The abraded area can be cleaned with any suitable solvent and allowed to dry. Fabricating further includes disposing an electrode onto a coating layer, such as an abraded area of the coating layer. An end portion of insulation of an electrical wire, such as wire

166, can be removed to form an exposed portion of the electrical wire. The exposed portion is then contacted with an electrode, followed by application of non-conductive tape and/or a protective coating, such as protective coating 412.

Electrodes (and coating layers) of the present disclosure may be disposed on a metal substrate or layer by any suitable deposition process. Deposition processes include screen printing and 3D printing. In addition, photolithography may be applied to a coating layer followed by deposition of an electrode into the photolithographed region of the layer.

An electrode, for example, may be deposited using any suitable screen printing apparatus supplied, for example, by ASM Assembly Systems of Munich, Germany. Screen printing can be performed using a screen having one or more openings shaped with the desired geometry for electrode formation. A deposition material may be placed onto a portion of the screen and then squeegeed across the opening with a squeegee. More specifically, the screen is located over and just above the surface to be printed so that ink can be accurately deposited in the desired position. The mesh of the screen is brought into contact with the surface by the squeegee as it is moved across the screen. Ink is pushed into the open area forming the pattern and the surplus is removed by the edge of the squeegee. The mesh should peel away from the surface immediately behind the squeegee, leaving all the ink that was in the mesh deposited on the printing surface. The screen can then be lifted clear. The recommended screen tension is the tension necessary to stretch the mesh sufficiently to cause the screen to peel away from the substrate after printing but not be stretched so much that damage occurs. The applied tension depends on the screen material, e.g. the extension used for nylon meshes is typically 6% and for polyester 3%. It is normal practice for the squeegee to be held at a 45° angle relative to the frame area.

An electrode, for example, may be deposited using any suitable 3D printing apparatus supplied, for example, by nScrypt, Inc. of Orlando, Fla. The nScript apparatus dispenses a conductive ink, e.g. DuPont CB230 silver-coated copper conductive ink or DuPont CB028 flexible silver ink, at a material flow rate that is adjusted by backpressure on the nozzle. The speed of the nozzle movement while patterning is constant, and the backpressure of the material in the nozzle is directly proportional to the flow rate. The nScrypt printing apparatus has a range of backpressures from 0 psi to about 30 psi. For the deposition of conductive ink onto coated panels, 18 psi backpressure can be used, which corresponds to a flow rate of about 0.052 grams/minute. After deposition of electrodes with the nScript apparatus, ink is baked for a fixed time at an elevated temperature to facilitate curing, e.g. 170° C. for 30 minutes.

A coating layer, for example, may be photolithographed using any suitable photolithography apparatus. Electrodes formed by photolithography are typically interdigitated electrodes.

Suitable interdigitated electrodes can be obtained from, for example, Synkera Technologies, Inc. of Longmont, Colo. or Micrux Technologies, S.L. of Oviedo, Spain.

Testing Methods

A material testing process such as a cyclic flexing fog spray process, for example, within apparatus 100, may be performed by exposing a material system, such as a panel, to a treating liquid, such as a salt fog, and flexing the material system. The exposing may be performed for from about 1 hour to about 4500 hours, such as about 200 hours to about 2000 hours, such as about 500 hours to about 1000 hours. Exposing a material system to a treating liquid for about 1 hour mimics, for example, salt fog exposure experienced by the material system as part of an aircraft in an arid climate. Exposing a material system to a treating liquid for about 4500 hours mimics, for example, salt fog exposure experienced by the material system as part of an aircraft in a very humid climate or a moderately humid climate for a prolonged period of time. The liquid may contain water that is reagent grade water. The liquid may be a salt solution. The salt solution may comprise sodium chloride. The salt solution may contain about 2 parts sodium chloride in 98 parts water to about 6 parts sodium chloride in 94 parts water, such as about 5 parts sodium chloride in about 95 parts water. The liquid, such as a salt solution, may contain less than about 0.1% of bromide, fluoride and iodide. The liquid, such as a salt solution, may contain less than about 1 ppm, such as about 0.3 ppm, by mass of copper. The liquid, such as a salt solution, might not contain anti-caking agents, as such agents may act as corrosion inhibitors. Material systems which may be tested include, for example, aircraft panels which may form the skins or fuselage of an aircraft, a coated lap joint between two metal panels, a wing-to-fuselage assembly, and combinations thereof. The liquid may be atomized to form the treating liquid, such as a salt fog, that may have a pH ranging from about 3 to about 11, such as about 5 to about 8, such as about 6.5 to about 7.2. pH may be measured using a suitable glass pH-sensing electrode, reference electrode, and pH meter system. It may be desirable to adjust the pH of the treating liquid. For example, a treating liquid having a low pH may mimic a polluted atmosphere containing acid rain and the like. Furthermore, pH of the liquid that is atomized into the treating liquid may be adjusted to recalibrate the liquid during an exposing process. pH may be adjusted by, for example, addition of hydrochloric acid (HCl) to decrease the pH or addition of sodium hydroxide (NaOH) to increase the pH. The liquid, such as a salt fog, may be flowed at a rate of about 0.5 milliliters per hour (mL/h) to about 5 mL/h per 80 $cm^2$ of horizontal collection area, such as about 1 mL/h to about 2 mL/h per 80 $cm^2$ of horizontal collection area. In at least one aspect, a material system, such as a panel, may be flexed by a fixture support using one of jaws 124*a-e* or by a plurality of jaws 124*a-e*. Flexing may be performed at varying frequencies to mimic the effect of mechanical stresses for corrosive conditions experienced by an aircraft material system under real world conditions. For example, a material system may be flexed at a frequency from about 0.1 Hertz (Hz) to about 150 Hz, about 0.1 Hz to about 100 Hz, about 0.1 Hz to about 60 Hz. Furthermore, the greater the curvature of a flexed material system, the greater the degradation to the material system using apparatus and methods of the present disclosure. For example, a flat panel having a length of 6 inches may be gripped by two jaws with a distance of 6 inches between the two jaws. The panel may be flexed at a rate of 0.33 Hz during exposure to a salt fog solution. In another example, a flat panel having a length of 7.5 inches may be gripped by two jaws also having a distance of 6 inches between the two jaws. The panel may be flexed at a rate of 0.33 Hz during exposure to a salt fog solution. The panel having a length of 7.5 inches has an increased curvature and undergoes increased degradation as compared to the panel having a length of 6 inches under otherwise identical conditions. Without being bound by theory, mechanical stresses that give curvature to a material system result in cracking of the material system which permits access of corrosive fluid, such as a salt fog, into a crack of the material system. After entering a crack of the material system, corrosive fluid may further enter between various additional layers (such as an underlying coating layer), if present. Accordingly, corrosive fluid may cause corrosion of the material system and/or one or more of the additional layers of the material system. Such conditions mimic the conditions experienced by an aircraft material system, such as a panel, during real world use.

In at least one aspect, an exposure zone, such as an enclosure 160 of apparatus 100, may be maintained at a temperature ranging from about −196° C. to about 100° C., −50° C. to about 95° C., 0° C. to about 50° C., such as about 33° C. to about 37° C., for example about 35° C., during the exposing of a material system to a treating liquid (such as a salt solution atomized into a salt fog), and/or the flexing the material system. The temperature may be monitored by a recording device or by a thermometer (not shown) that can be read from an outside surface of apparatus 100. In at least one aspect, exposing a material system, such as a panel, to a liquid, such as a salt fog, and flexing the material system may be performed concurrently. In at least one aspect, exposing a material system, such as a panel, to a liquid, such as a salt fog, and flexing the material system may be performed sequentially. In at least one aspect, a material system may be exposed to a salt fog and flexed concurrently as well as sequentially, which provides recreation of an irregular or variable flight-specific strain profile that may be experienced by a material system in service. In at least one aspect, exposing a material system to a liquid and/or flexing the material system may be interrupted to visually inspect, rearrange, or remove the material system, and/or replenish a solution, such as a solution in liquid reservoir 104.

Before, during (in situ), and/or after flexing and spraying, the impedance of one or more layers of the material system can be measured using an electrochemical impedance spectrometer. Electrochemical impedance spectroscopy (EIS) provides in situ measurements of impedance of one or more layers of the material system. The measurements provide information for determining coating properties, such as coating degradation, corrosion at the substrate/coating interface, and absorbed moisture over a period of time. Electrochemical impedance spectroscopic processes of the present disclosure can be performed at an excitation potential of from about 5 mV to about 150 mV, such as about 10 mV to about 20 mV. Electrical frequencies for EIS may be from about 0.1 Hz-10,000 Hz, such as from about 1 Hz to about 5,000 Hz, such as from about 1 Hz to about 100 Hz, such as about 0.01 Hz to about 10 Hz, or from about 100 Hz to about 4,000 Hz. In at least one aspect, EIS is performed continuously at a set interval and fixed frequency from about 0.5 Hz to about 100 Hz, such as from about 1 Hz to about 10 Hz.

In the following examples, a material system measuring 3.75 inches wide by 14.5 inches long was secured by two jaws in a fixture support in the device described in FIG. 1. While flexing the panel at about 1 Hz, the panel was exposed to a sodium chloride salt fog (pH 6.8) for several days.

EXAMPLE 1

Material System Having Conventional Interdigitated Electrodes

Using conventional interdigitated electrodes, resistance is typically measured between the metal interdigitated electrode and underlying substrate as they corrode. In that case, thicker electrodes work better because the electrode is corroded during the process. If the electrode is too thin, the electrode will corrode away over time during testing.

For this example, interdigitated electrodes were secured to a top surface and bottom surface of a coated aluminum coupon using double sided tape. The electrodes were masked with plater's tape. A chromated primer coating was applied to the coupon (including the electrode-areas). The plater's tape was removed once the coating had cured. Wires were soldered to the electrodes. The electrodes and wire were then insulated with a 2-part epoxy and allowed time to cure to form the completed material system. Corrosion testing was performed within a cyclic corrosion chamber as described above using ASTM B117. EIS was performed at 150 mV excitation potential, 10 Hz-10,000 Hz frequency range, and was performed continuously at a set interval and fixed frequency of 1 Hz.

Figure 8:
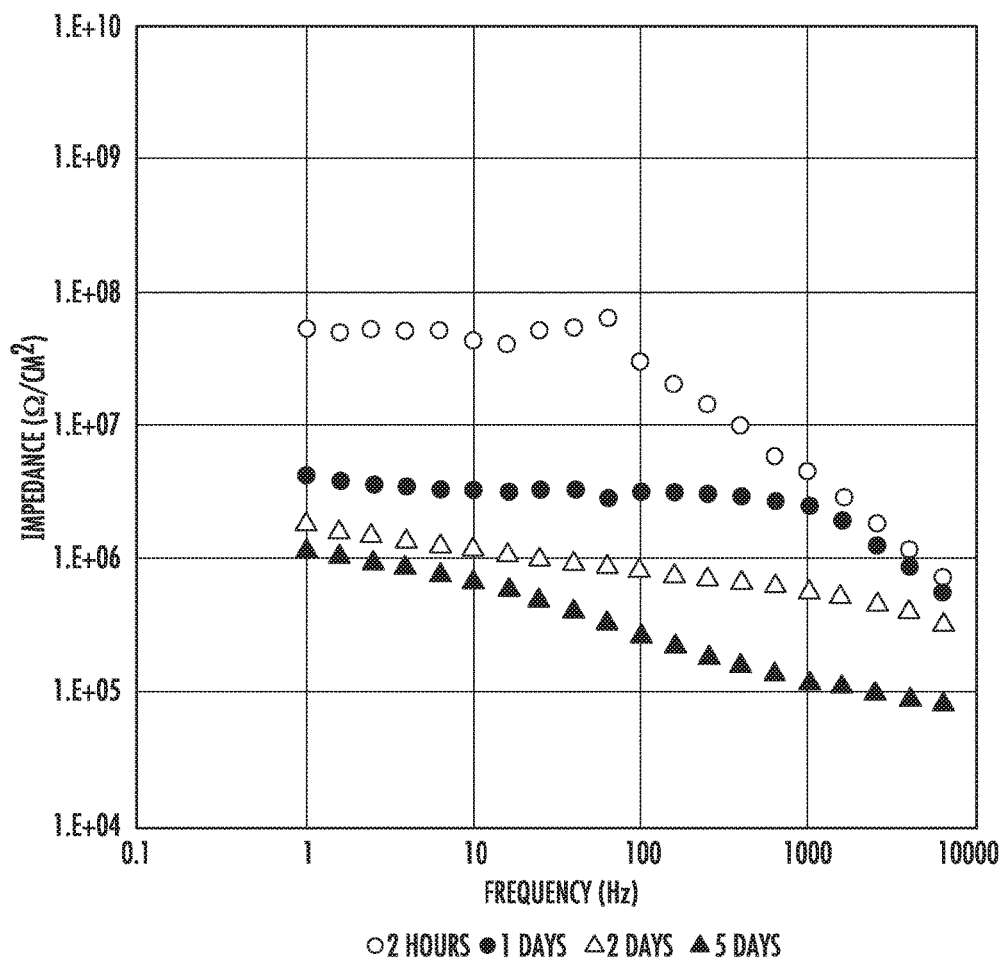
FIG. 8 is a graph of impedance data of a material system comprising an interdigitated electrode pair of Example 1 disposed onto a coating material.

FIG. 8 is a graph of impedance data of a material system comprising interdigitated electrodes of Example 1. The material system was exposed to salt fog for 5 days. As shown in FIG. 8, impedance decreases over time upon moisture ingress into the material system. It was observed that the interdigitated electrodes cause a defect zone in the coating. Furthermore, the values of the data observed are indicative of the actual impedance of only the coating disposed over the electrodes, area surrounding the electrodes and coupon (due to the application of double sided tape for adhering the electrodes to the coupon).

EXAMPLE 2

Material System Having Thin Circular Electrodes Formed by a Dispensing Gun

A bottom and top surface of a coated aluminum coupon was lightly abraded, and cleaned with a solvent and allowed to dry. Electrodes were formed on the abraded areas using a conductive silver epoxy to a thickness of less than about 12 μm that was applied to a surface using a dispensing gun. Each electrode had a contact surface area of 1 cm$^2$ and a circular shape. Approximately 0.5 cm of insulation was stripped from a thin gauge wire, and the wire was taped to the coupon so that the exposed piece of wire was laying flat across the electrode application site. A 2-part waterproof epoxy was used as a protective coating to electrically and physically isolate the electrodes from the environment to form the completed material system. Corrosion testing was performed within a cyclic corrosion chamber as described above using ASTM B117. EIS was performed at 150 mV excitation potential, 10 Hz-10,000 Hz frequency range, and was performed continuously at a set interval and fixed frequency of 1 Hz.

Figure 9:
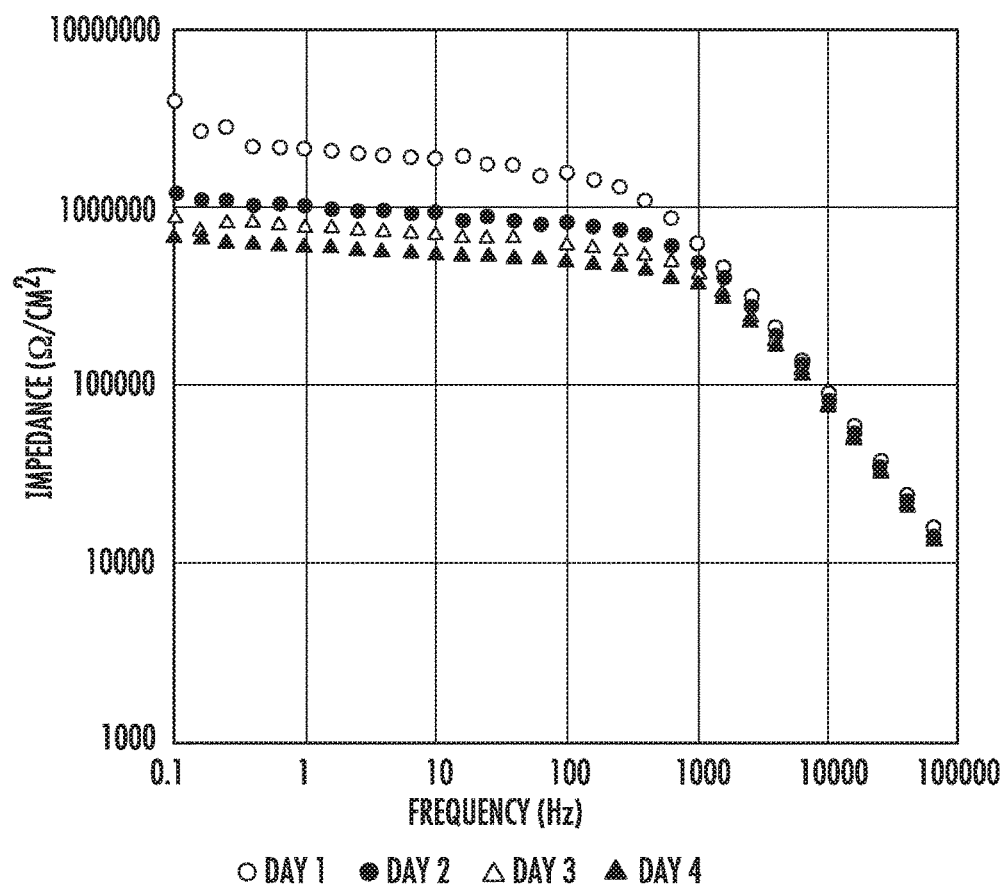
FIG. 9 is a graph of impedance data of a material system comprising electrodes of Example 2, according to an aspect of the present disclosure.

FIG. 9 is a graph of impedance data of a material system comprising thin electrodes of Example 2, according to an aspect of the present disclosure. The material system was exposed to salt fog for 4 days. As shown in FIG. 9, impedance decreases over time upon moisture ingress into the material system. Unlike coupons having conventional interdigitated electrodes, the electrodes did not release from the coupon surface in the absence of adhesive during testing and did not substantially corrode during testing.

EXAMPLE 3

Scribed Material System Having Thin Circular Electrodes Formed by a Dispensing Gun A bottom and top surface of a scribed coated aluminum coupon was lightly abraded and cleaned with a solvent and allowed to dry. Electrodes were formed on the abraded areas to a thickness of less than about 12 μm using a conductive silver epoxy that was applied to a surface using a dispensing gun. Each electrode had a contact surface area of 1 cm$^2$ and a circular shape. Approximately 0.5 cm of insulation was stripped from a thin gauge wire, and the wire was taped to the coupon so that the exposed piece of wire was laying flat across the electrode application site. A 2-part waterproof epoxy was used as a protective coating to electrically and physically isolate the electrodes from the environment to form the completed material system. Corrosion testing was performed within a cyclic corrosion chamber as described above using ASTM B117. EIS was performed at 150 mV excitation potential, 0.1 Hz-10,000 Hz frequency range, and was performed continuously at a set interval and fixed frequency of 1 Hz.

Figure 10:
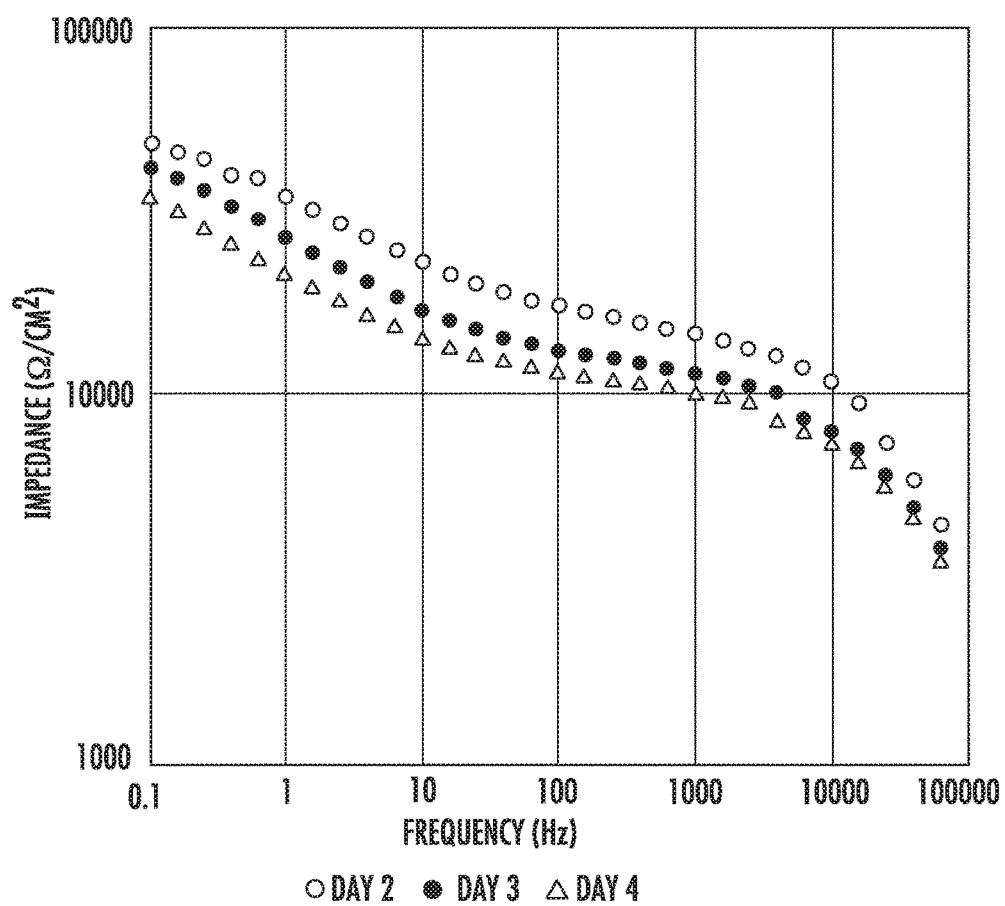
FIG. 10 is a graph of impedance data of a scribed material system comprising electrodes of Example 3, according to an aspect of the present disclosure.

FIG. 10 is a graph of impedance data of a scribed material system comprising thin electrodes of Example 3, according to an aspect of the present disclosure. The material system was exposed to salt fog for 4 days. As shown in FIG. 10, impedance decreases over time upon moisture ingress into the material system. Unlike coupons having conventional interdigitated electrodes, the electrodes did not release from the coupon surface in the absence of adhesive during testing and did not substantially corrode during testing.

EXAMPLE 4

Material System Having Embedded Thin Rectangular Electrodes Formed by Screen Printing Rectangular electrodes were screen printed to a thickness of less than about 12 μm onto a top surface and bottom surface of an anodized and painted aluminum coupon. The electrodes were fabricated from Ag-530 ink manufactured by Conductive Compounds. Wire leads were soldered to the electrodes, and the electrodes and wire leads were sealed with non-conductive epoxy. A boric sulfuric acid anodized (BSAA) primer coating was applied to the coupon (including the electrode areas) to form the completed material system. Corrosion testing was performed within a cyclic corrosion chamber as described above using ASTM B117. EIS was performed at 150 mV excitation potential, 10 Hz-10,000 Hz frequency range, and was performed continuously at a set interval and fixed frequency of 1 Hz.

Figure 11:
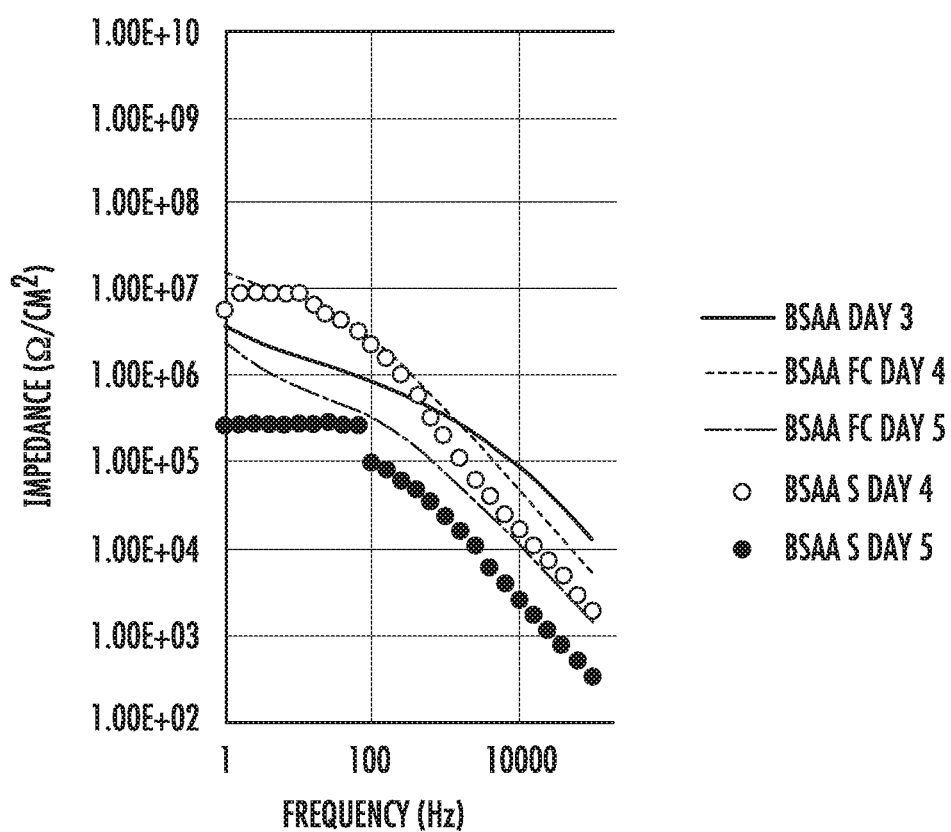
FIG. 11 is a graph of impedance data of a material system comprising electrodes of Example 4, according to an aspect of the present disclosure.

FIG. 11 is a graph of impedance data of a material system comprising thin electrodes of Example 4, according to an aspect of the present disclosure. The material system was exposed to salt fog for 5 days. Flat cell (FC) measurements and sensor (S) measurements were performed. Flat cell measurements involve the use of a specialized electrochemical cell filled with salt solution. This creates a "bulk electrolyte" on top of the coating. With the embedded sensor measurements, we are conducting EIS in a salt spray chamber which mimics atmospheric exposures. Salt fog leaves thin films of electrolyte on the coated surface. Thin films and bulk electrolytes have different diffusion properties, which can impact corrosion kinetics and absorption of moisture into the coatings. This can cause slight differences in the EIS spectrum. Thus, the EIS spectra from the sensors are compared to those in a flat cell because flat cell techniques are standardized. The feasibility and novelty of performing EIS is demonstrated with embedded electrodes by showing that these sensors give nearly-equivalent data as a flat cell experiment without having to use a specialized test cell or take the articles out of the chamber for analysis.

As shown in FIG. 11, impedance decreases over time upon moisture ingress into the material system. Unlike coupons having conventional interdigitated electrodes, a defect zone in the coating was not formed (1) in a material system having thin electrodes formed by screen printing and (2) in the absence of adhesive between the electrodes and the coupon surface.

EXAMPLE 5

Material System Having Thin Electrodes Formed by 3D Printing

A chromated primer coating was applied to a coupon, followed by an epoxy coating deposited on the chromated primer. The epoxy coated aluminum coupon was not abraded, and two electrodes were disposed onto a top surface of a coupon and two electrodes were disposed onto a bottom surface of the coupon, each electrode disposed to a thickness of less than about 12 μm using an nScrypt 3D printer. Electrode material was Dupont CB230 ink, which is a silver coated copper conductive material. Wire leads were soldered to the electrodes. The electrodes and leads were sealed with non-conductive epoxy to form the completed material system. Corrosion testing was performed within a cyclic corrosion chamber as described above using ASTM B117. EIS was performed at 150 mV excitation potential, 10 Hz-10,000 Hz frequency range, and was performed continuously at a set interval and fixed frequency of 1 Hz.

Figure 12:
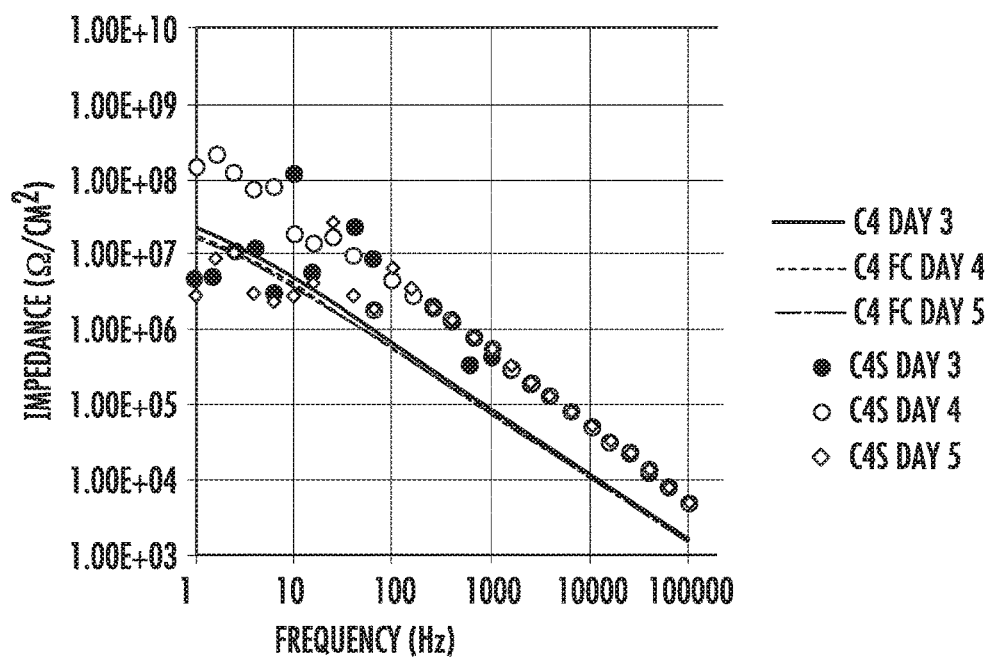
FIG. 12 is a graph of impedance data of a material system comprising electrodes of Example 5, according to an aspect of the present disclosure.

FIG. 12 is a graph of impedance data of a material system comprising thin electrodes of Example 5, according to an aspect of the present disclosure. The material system was exposed to salt fog for 5 days. Flat cell (C4 FC) measurements and sensor (C4 S) measurements were performed. As shown in FIG. 12, impedance decreases over time upon moisture ingress into the material system. Unlike coupons having conventional interdigitated electrodes, the electrodes did not release from the coupon surface in the absence of adhesive during testing and did not substantially corrode during testing. Unlike coupons having conventional interdigitated electrodes, a defect zone in the coating was not formed (1) in a material system having thin electrodes formed by 3D printing and (2) in the absence of adhesive between the electrodes and the coupon surface.

Material systems, apparatus and methods of the present disclosure provide a controlled salt fog environment and monitoring of material performance, such as corrosion, on a variety of material systems, such as aircraft material systems, such as panels, coated lap joints between two or more panels, wing-to-fuselage assemblies, or combinations thereof. Material systems, apparatus and methods of the present disclosure provide an ability to replicate in-service, real-world failure modes and mechanisms in a controlled exposure environment.

Mechanical flexing of a material system in an apparatus of the present disclosure may result in increased corrosion of a material system. The compounding effects of mechanical and chemical stresses combine to induce corrosion, which more accurately replicates corrosion experienced by a material system, such as an aircraft panel, in a real-world environment. Accordingly, material systems, methods and apparatus of the present disclosure more accurately simulate the corrosion observed with aircraft material systems during real-world use of the aircraft. Material systems, methods and apparatus of the present disclosure allow for testing corrosion of stand-alone material systems and the interfaces between coating layers, which more accurately represents the corrosion experienced by material systems, such as panels, during actual use of the material systems as part of an aircraft. Material systems, methods and apparatus of the present disclosure further provide re-creation of irregular flight-specific strain profiles so that improved predictive as well as forensic investigations of aircraft material systems may be performed.

Material systems, methods and apparatus of the present disclosure provide electrochemical monitoring of a coating during outdoor exposure, accelerated testing in an environmental chamber, and electrochemical monitoring of material systems while in use (e.g, in situ). In situ electrochemical monitoring provides assessment of the integrity of a material system without visual inspection of the material system and does not require stoppage of a flexing and/or salt fog exposure of the material system. Material systems of the present disclosure further provide thin electrodes which can be located on an outer surface of a material system or embedded within the material system (e.g., disposed between two layers). Such material systems reduce or eliminate defect zones in a coating disposed on the electrode-area of the material system. Furthermore, material systems of the present disclosure further provide reduced or eliminated adhesive use between the electrode and an underlying substrate which provides accurate electrochemical data from a spectrometer during testing. Material systems of the present disclosure further provide electrodes with reduced or eliminated corrosion during testing. Material systems of the present disclosure further provide electrodes that can be shaped to provide a controllable contact surface area for desired electrochemical applications.

While the foregoing is directed to aspects of the present disclosure, other and further aspects of the present disclosure may be devised without departing from the basic scope thereof. Furthermore, while the foregoing is directed to material systems, such as aircraft material systems, such as panels, coated lap joints between two or more panels, and wing-to-fuselage assemblies, aspects of the present disclosure may be directed to other material systems not associated with an aircraft, such as a multicomponent material system used in aerospace, automotive, marine, energy industry, and the like.

What is claimed is:

1. A method for determining material performance comprising:
    flexing a material system,
    the material system comprising:
        a metal substrate,
        a first coating layer disposed on the metal substrate,
        a first electrode directly disposed on the first coating layer, and
        a second electrode disposed on the metal substrate; and
    detecting impedance of the material system with an electrochemical impedance spectrometer.

2. The method of claim 1, further comprising exposing the material system to salt fog.

3. The method of claim 2, wherein detecting is performed concurrently with flexing the material system and exposing the material system to salt fog.

4. The method of claim 1, wherein detecting is performed concurrently with flexing the material system.

5. The method of claim 1, wherein detecting comprises exciting the second electrode at an excitation potential from about 5 mV to about 150 mV.

6. The method of claim 1, wherein detecting is performed continuously at a set interval and fixed frequency from about 0.01 Hz to about 10 Hz.

7. The method of claim 2, wherein flexing is performed at a frequency from about 0.1 Hz to about 60 Hz.

8. The method of claim 3, wherein flexing the material system and exposing the material system are performed concurrently.

9. The method of claim 2, wherein flexing the material system and exposing the material system are performed sequentially.

10. The method of claim 2, wherein exposing the material system and flexing the material system are performed in the same chamber.

11. The method of claim 1, wherein the first electrode or the second electrode has one or more spokes extending therefrom.

* * * * *